United States Patent
Liu et al.

(10) Patent No.: US 12,240,481 B2
(45) Date of Patent: Mar. 4, 2025

(54) METHOD AND DEVICE FOR INTELLIGENT HEALTH MANAGEMENT OF A CABIN OF A VEHICLE

(71) Applicant: Mercedes-Benz Group AG, Stuttgart (DE)

(72) Inventors: Dawei Liu, Beijing (CN); Meijing Li, Beijing (CN)

(73) Assignee: Mercedes-Benz Group AG, Stuttgart (DE)

( * ) Notice: Subject to any disclaimer, the term of this patent is extended or adjusted under 35 U.S.C. 154(b) by 0 days.

(21) Appl. No.: 18/695,244

(22) PCT Filed: Aug. 30, 2022

(86) PCT No.: PCT/CN2022/115727
§ 371 (c)(1),
(2) Date: Mar. 25, 2024

(87) PCT Pub. No.: WO2023/045717
PCT Pub. Date: Mar. 30, 2023

(65) Prior Publication Data
US 2024/0270274 A1    Aug. 15, 2024

(30) Foreign Application Priority Data

Sep. 26, 2021 (CN) .......................... 202111127952.6

(51) Int. Cl.
*B60Q 1/00* (2006.01)
*B60W 30/182* (2020.01)
*B60W 40/08* (2012.01)
*B60W 50/00* (2006.01)
*B60W 50/14* (2020.01)

(52) U.S. Cl.
CPC .......... *B60W 50/14* (2013.01); *B60W 30/182* (2013.01); *B60W 40/08* (2013.01);
(Continued)

(58) Field of Classification Search
CPC .... B60W 50/14; B60W 30/182; B60W 40/08; B60W 50/0098; B60W 2050/146;
(Continued)

(56) References Cited

U.S. PATENT DOCUMENTS 7,348,880 B2 *  3/2008  Hules ................. B60R 25/1004
                                                   340/425.5
9,988,055 B1 *  6/2018  O'Flaherty ............ G08B 21/06
(Continued)

FOREIGN PATENT DOCUMENTS

CN      108254199 A      7/2018
CN      110268451 A      9/2019
(Continued)

OTHER PUBLICATIONS

International Search Report (PCT/ISA/210) issued in PCT Application No. PCT/CN2022/115727 dated Nov. 29, 2022 (2 pages).
(Continued)

*Primary Examiner* — Anh V La
(74) *Attorney, Agent, or Firm* — Crowell & Moring LLP

(57) ABSTRACT

A method for intelligent health management of a cabin of a vehicle includes acquiring health level information related to a health status of a user in the cabin, acquiring operating preference data of the user for at least one in-vehicle function, analyzing a correlation between the operating preference data of the user for the at least one in-vehicle function and the health level information within a determined time period, and presenting a result of the analyzing to the user.

16 Claims, 8 Drawing Sheets

(52) U.S. Cl.
CPC ... *B60W 50/0098* (2013.01); *B60W 2050/146* (2013.01); *B60W 2540/043* (2020.02); *B60W 2540/221* (2020.02); *B60W 2556/05* (2020.02)

(58) Field of Classification Search
CPC ..... B60W 2540/043; B60W 2540/221; B60W 2556/05; G16H 40/63; G16H 50/20; G16H 50/30
USPC ........ 340/425.5, 438, 439, 449, 457, 426.22
See application file for complete search history.

(56) References Cited

U.S. PATENT DOCUMENTS

| 2010/0182137 | A1* | 7/2010 | Pryor | B60K 35/10 |
| | | | | 340/425.5 |
| 2018/0194360 | A1* | 7/2018 | Hill | B60W 50/14 |
| 2019/0061772 | A1* | 2/2019 | Prinz | B60K 28/06 |
| 2019/0073547 | A1* | 3/2019 | el Kaliouby | G06N 3/084 |
| 2020/0342993 | A1 | 10/2020 | Vandewall et al. | |
| 2020/0353940 | A1* | 11/2020 | Kim | B60H 1/00742 |

FOREIGN PATENT DOCUMENTS

| CN | 111452747 A | 7/2020 |
| CN | 111655135 A | 9/2020 |

OTHER PUBLICATIONS

International Preliminary Report on Patentability (PCT/IPEA/409) issued in PCT Application No. PCT/CN2022/115727 dated Nov. 2, 2023 (3 pages).

* cited by examiner

METHOD AND DEVICE FOR INTELLIGENT HEALTH MANAGEMENT OF A CABIN OF A VEHICLE

BACKGROUND AND SUMMARY OF THE INVENTION

This disclosure relates to a method for intelligent health management of a cabin of a vehicle, a device for intelligent health management of a cabin of a vehicle, and a computer program product.

With the continuous progress of vehicle intelligence, various human-machine interaction functions equipped by vehicles have contributed to the safe driving and the improved comfort of drivers. At present, however, phenomena of environmental pollution are gradually increasing, and vehicle users are spending longer time staying in the vehicle. Therefore, the environmental health in the cabin of the vehicle is as well an issue worth paying attention to.

In order to solve this problem, it is proposed in the prior art to monitor the air quality in the vehicle in real time, and guide the user with voice prompts to perform relevant operations to improve the level of air quality in the vehicle. A method for controlling in-vehicle air environment is also known, in which method a corresponding odor control strategy is invoked as a function of the environment where the vehicle is located, and vehicle-mounted air conditioning equipment is regulated according to the odor control strategy, so that the air in the vehicle can be intelligently processed as a function of the scene.

However, the aforementioned current solutions still have many shortcomings, in particular in that these known monitoring solutions can only conduct simple collection and report of indoor environmental parameters, but cannot let users know which operating habits they have in the vehicle will produce which kind of influence on the environmental health in the vehicle. In addition, when facing highly individualized user groups, uniformly formed adjustment measures are incapable of accurately meeting the preferences of different users.

Given such background, it is expected to provide an improved intelligent health management solution for the cabin of the vehicle, so that the environmental health in the cabin can be intelligently analyzed in a comprehensive and integrated manner in conjunction with different operating habits of individual users.

The objective of the disclosure is to provide a method for intelligent health management of a cabin of a vehicle, a device for intelligent health management of a cabin of a vehicle, and a computer program product, so that at least some of the problems in the prior art can be solved.

According to a first aspect of the disclosure, a method for intelligent health management of a cabin of a vehicle is provided, the method comprising the steps of:

S1: acquiring health level information related to a health status of a user in the cabin;

S2: acquiring operating preference data of the user for at least one in-vehicle function; and S3: analyzing a correlation between the operating preference data of the user for the at least one in-vehicle function and the health level information within a determined time period, and presenting a result of the analysis to the user.

The disclosure in particular contains the following technical idea: by means of integrating fragmented operating behaviours of the user in the cabin and establishing a connection with the environmental health in the vehicle, the vehicle user is allowed not only to know the environmental health level in the cabin, but also to understand the influence of his own vehicle-use habits on the health level. In this way, the monitored health indicators are provided with contextual meanings, so that the vehicle is no longer a point-to-point carrier, but carrying the function of communicating and interacting with the user.

Optionally, health level information is acquired in the form of a raw sensor signal and/or a grading result of the raw sensor signal.

Such an embodiment offers in particular the following advantages: by recording raw sensor signals, a simple way of environmental monitoring of the cabin is allowed, thus enabling a lower energy consumption associated therewith or a possibility of applying resources to other functions. Through the grading processing of raw sensor signals, the quality status of the health level of the cabin and fluctuations thereof can be more clearly conveyed, which is advantageous to the subsequent correlation analysis and data presentation.

Optionally, health level information comprises environmental level information and biological level information, the environmental level information particularly comprising temperature in the cabin, air quality in the cabin, pollen concentration in the cabin, ultraviolet index in the cabin, oxygen concentration in the cabin, and humidity in the cabin, and the biological level information particularly comprising infrared vital signs, degree of attention, and visual fatigue of the user.

Such an embodiment offers in particular the following advantages: the health level in the cabin can be reflected not only by environmental factors, but also by physical and mental states of the user. Therefore, by acquiring information in the above two aspects, the health level in the cabin can be analyzed more comprehensively and effectively.

Optionally, the operating preference data comprises: number of times of activation, duration of use, frequency of use, time period of use, operating mode, operating temperature, operating angle, and operating intensity of at least one in-vehicle function by the user under corresponding external environmental conditions.

Such an embodiment offers in particular the following advantages: by extracting existing functional data of the vehicle, software and hardware that have already been installed in the vehicle become active sources for data reception and analysis, thereby allowing the user to fully understand his own operating habits and operating patterns of in-vehicle functions.

Optionally, step S3 comprises:

pre-assigning an impact score on the health level information to different operating states of each in-vehicle function;

calculating a cumulative impact score of each in-vehicle function under the consideration of the operating preference data of the user; and determining the correlation based on the cumulative impact score.

Such an embodiment offers in particular the following advantages: the correlation between different operating states of each in-vehicle function and the health level can be quantified, and the statistical results can be used to more effectively analyze the degree of influence of different factors on the health level, thereby formulating adjustment strategies in a more targeted manner.

Optionally, step S3 comprises:

presenting a degree of positive contribution and/or a degree of negative contribution of the operating preference data of the user to the health level information for different in-vehicle functions.

Such an embodiment offers in particular the following advantages: in this way, the user is allowed to know which of his operating behaviors degrade the health level in the cabin, and which operating habits have a positive effect on the health level and thus can be preserved. Hence, such instructive information is beneficial to a more targeted adjustment of the operating behaviors of the user during the future use of the vehicle.

Optionally, step S3 comprises:
presenting separately the correlation between the operating preference data of the user for each in-vehicle function and the health level information; and/or
presenting synergistically the correlation between the operating preference data of the user for a plurality of in-vehicle functions and the health level information.

Such an embodiment offers in particular the following advantages: the separate presentation can reflect the impact of each operating behavior on a specific health indicator more clearly, thereby allowing specific operation behaviors to be controllable. The synergistic presentation further takes into account logical and temporal correlations between different in-vehicle functions or different operating states of the in-vehicle functions, so it can reflect a combined action of multiple interactive functions in an integrated manner, which makes the subsequent adjustment more precise.

Optionally, step S3 comprises: presenting the correlation in different time dimensions, wherein the correlation is presented in a time dimension in particular in the form of days, weeks, months, quarters and/or years.

Such an embodiment offers in particular the following advantages: the recording and presenting manner in different time dimensions can reflect temporal changes of the behavioural habits of the user and the health level in the cabin and visualize such changes. It thus is convenient for the user to know short-term and long-term characteristics of his operating behaviors, and the time factor can be taken into account for the future behavioural planning.

Optionally, the method further comprises the following steps:
generating an adjustment strategy for at least one in-vehicle function according to the operating preference data and the health level information within a determined time period; and
presenting the adjustment strategy to the user and/or automatically adjusting at least one in-vehicle function with the adjustment strategy.

Such an embodiment offers in particular the following advantages: for formulation of future adjustment strategies or generation of rationalization suggestions, it is aimed not only at stabilizing the health level in the cabin within a reasonable range, but also at taking into account usage habits and preferences of the user for various in-vehicle functions. A tailored in-vehicle health management solution is thereby provided for the user, which improves user satisfaction.

Optionally, at least one in-vehicle function is automatically adjusted with the adjustment strategy only when a user confirmation of the adjustment strategy is received.

Here, the following technical advantage is in particular achieved: the user is left with enough autonomy for choice making, which improves user experience.

Optionally, a usage habit model of the user for at least one in-vehicle function is trained by means of the operating preference data of the user and the health level information in the cabin, and the trained usage habit model is used for predicting: operating preference data that enables the health level information in the cabin to meet preset conditions under corresponding external environmental conditions, and an adjustment strategy for at least one in-vehicle function is generated based on the predicted operating preference data.

Such an embodiment offers in particular the following advantages: through the establishment of a self-learning model, the in-vehicle adjustment system is allowed to simulate perceptual mechanisms in the brain of the user so as to predict an adjustment manner that meets health requirements and meanwhile meets as much as possible the expectation of the user. This can reduce manual operations of the in-vehicle functions by the vehicle user to a certain extent, so that the user can focus more on his driving behavior.

Optionally, prior to training the usage habit model by means of the operating preference data of the user and the health level information in the cabin, the usage habit model has been pre-trained based on big data, in particular by means of crowdsourced operating preference data of user groups of a specific geographic region and/or of a specific season and/or of a specific gender and/or of a specific age as well as corresponding crowdsourced health level information.

Such an embodiment offers in particular the following advantages: by pre-training a machine learning model with the help of big data in advance, an initial framework of a parametric model can be quickly established on the basis of making full use of the prior knowledge accumulated in the past, and then the parametric model can be finely adjusted based on the specific user habits and preferences, thereby speeding up the convergence process of algorithm training. Since an overall framework of the parametric model has been estimated, which only needs to be calibrated in the details, the expenditure of time during the primary learning stage is greatly reduced, and user satisfaction is improved. In addition, user groups with the same factors, such as the same region, season, cultural background, and gender, may share common features in terms of operating habits, and a clustering training manner can better match the output results with the user habits.

Optionally, the adjustment strategy is generated with a first mode and/or a second mode. In the first mode, usage habits of the user are classified based on the operating preference data of the user, and a predefined adjustment strategy is retrieved according to a result of the classification; and in the second mode, it is checked whether there is a deviation between the predefined adjustment strategy and the usage habits of the user, and the predefined adjustment strategy is corrected in response to the deviation so as to reduce the deviation.

Such an embodiment offers in particular the following advantages: by pre-storing adjustment strategies and directly classifying the same according to user habits, a suitable adjustment strategy can be quickly located, and the expenditure of time in repeated adjustment can also be saved, which is especially advantageous to users with relatively stable operating habits. By learning in the manner of feedback, the adjustment process can be carried out in a more targeted manner, so that the adjustment strategy continuously gets close to the expectation of the user in an iterative process, and this is particularly advantageous to users with highly random operating habits.

Optionally, it is checked whether there is the deviation by recording a feedback event of the user on the adjustment strategy, and the feedback event comprises: a manual adjustment of the operating state of at least one in-vehicle function by the user.

Such an embodiment offers in particular the following advantages: the number of times and the degree of manual intervention by the user can reflect his degree of satisfaction with a currently applied automatic adjustment strategy, so such a feedback event can be re-used as supplementary training data to update internal parameters of the machine learning model, thereby continuously optimizing the finally obtained training result.

Optionally, the method further comprises the steps of: storing the adjustment strategy in the cloud and/or locally for an identity of the user, and retrieving a corresponding adjustment strategy from the cloud and/or locally when the identity of the corresponding user is identified.

Such an embodiment offers in particular the following advantages: through this retrieval process, a matching automatic adjustment strategy can be applied directly to the user identity in the next usage cycle or re-training can be performed directly on the basis of the last training result, without the need to start from the very beginning for a self-adaptive process. User satisfaction is thus improved.

According to a second aspect of the disclosure, a device for intelligent health management of a cabin of a vehicle is provided, which is used for performing the method according to the first aspect of the disclosure, the device comprising:
 a first acquisition module, which is configured to acquire health level information related to a health status of a user in the cabin;
 a second acquisition module, which is configured to acquire operating preference data of the user for at least one in-vehicle function; and
 an analysis module, which is configured to analyze a correlation between the operating preference data of the user for at least one in-vehicle function and the health level information within a determined time period, and to present a result of the analysis to the user.

According to a third aspect of the disclosure, a computer program product is provided, wherein the computer program product comprises a computer program for implementing the method according to the first aspect of the disclosure when being executed by a computer.

The disclosure will be described in greater detail with reference to the accompanying drawings, which leads to a better understanding of the principles, characteristics and advantages of the disclosure.

DETAILED DESCRIPTION OF THE DRAWINGS

For a clearer understanding of the technical problems to be solved, the technical solutions and advantageous technical effects of the disclosure, the disclosure now will be further explained in details in combination with the accompany drawings and a number of exemplary embodiments. It should be understood that the particular embodiments described herein are merely for the purpose of explaining the disclosure, rather than limiting the scope of protection of the disclosure.

Figure 1:
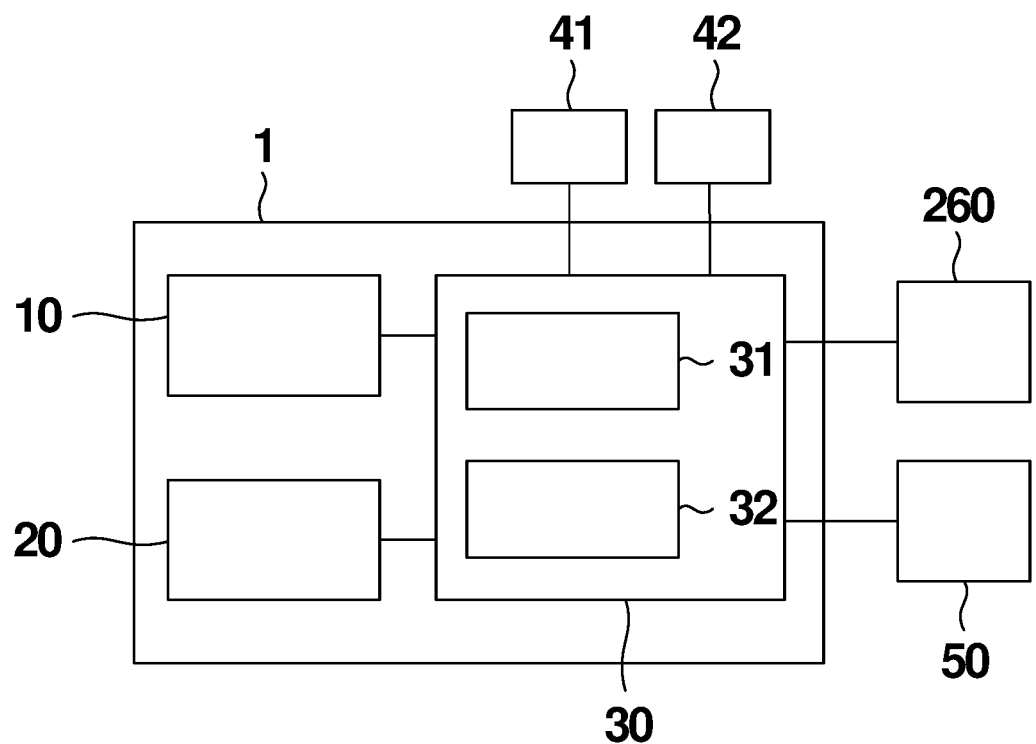
FIG. 1 shows a block diagram of a device for intelligent health management of a cabin of a vehicle according to an exemplary embodiment of the disclosure.

FIG. 1 shows a block diagram of a device for intelligent health management of a cabin of a vehicle according to an exemplary embodiment of the disclosure. A device 1 comprises a first acquisition module 10, a second acquisition module 20 and an analysis module 30.

The first acquisition module 10 is used for acquiring health level information related to a health status of a user in the cabin. Here, the first acquisition module 10 may, for example, be configured as a communication interface and thus be able to receive raw sensor signals measured in real-time from various sensors arranged on the vehicle. In addition, the first acquisition module 10 may also receive a grading result of the raw sensor signals and take it as health level information. It is also conceivable that the first acquisition module 10 is, for example, directly configured as a sensor which comprises an associated processing unit, so that various signals in the cabin can be directly detected thereby and health level information can be provided. In the sense of the disclosure, the raw sensor signal refers to, for example, an absolute sensor parameter that can be measured directly by a sensor, comprising, for example, temperature, air quality index, humidity, content of a certain gas in the air, and the like. A grading evaluation result refers to, for example, a result of pre-processing of the raw sensor signal by means of a threshold or other evaluation indexes. For example, after the air quality index in the vehicle within a period of time has been collected, it can be classified with the help of an air quality threshold, thereby obtaining the air quality status within the period of time.

The second acquisition module 20 is used for acquiring operating preference data of the user for at least one in-vehicle function. Here, the second acquisition module 20 may also be configured, for example, as a communication interface and thus can receive data from various software and hardware of the vehicle so as to use the date for the analysis of operating behaviors of the user.

The analysis module 30 is connected to the first acquisition module 10 and the second acquisition module 20, in order to receive the operating preference data of the user and the health level information in the cabin, respectively. For the convenience of functional assignment, the analysis module 30 further comprises a report generating unit 31 and a strategy generating unit 32. In the report generating unit 31, for example, the operating preference data and the health level information within a determined period of time can be extracted and the correlation between the two can be analyzed. In the strategy generating unit 32, for example, an adjustment strategy or rationalization suggestion for at least one in-vehicle function can be generated based on historical operating preference data and health level information. In this exemplary embodiment, the analysis module 30 is further connected to an external environment sensor 41 and a user identity input device 42 to output a suitable adjustment strategy as a function of real-time environmental changes outside the vehicle, and to allow retrieval of a corresponding adjustment strategy according to an identity of the user. In addition, the analysis module 30 is, for example, further in communication connection with a mobile terminal 260 of the user, so that the analysis result can be presented to the user in the form of an intelligent analysis report of the cabin. In addition, the analysis module 30 is, for example, also in communication connection with at least one actuator 50 of the vehicle, in order to control the operation of the at least one actuator according to the generated adjustment strategy.

Figure 2:
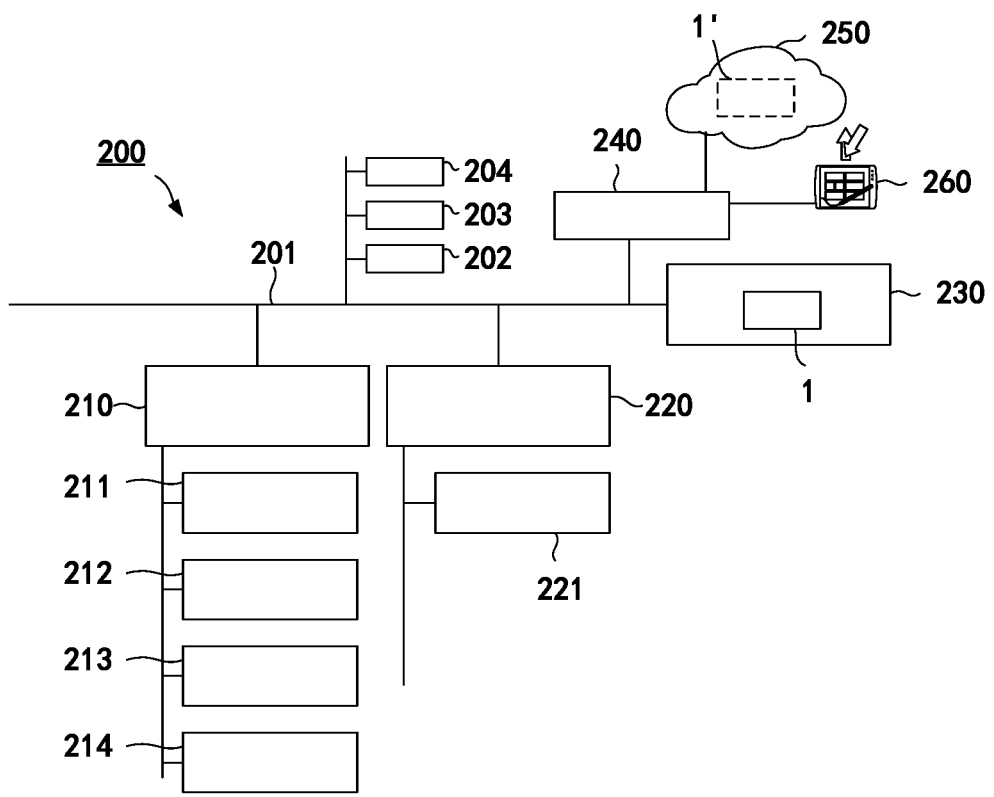
FIG. 2 shows a schematic diagram of an electrical electronic architecture of a vehicle according to an exemplary embodiment of the disclosure.

FIG. 2 shows a schematic diagram of an electrical electronic architecture of a vehicle according to an exemplary embodiment of the disclosure.

An electrical electronic architecture 200 comprises a vehicle bus 201 and a plurality of domain controllers 210, 220, 230 communicatively coupled to the vehicle bus 201. Here, the vehicle bus 201 comprises, for example, a LIN bus, a CAN bus, an Ethernet bus, a FlexRay bus, etc.

The domain controller 210 for a body domain is, for example, connected to a plurality of interior trim and exterior trim modules of a vehicle body, which modules comprise, for example, a vehicle window module 211, an ambient lighting module 212, a seat adjustment module 213, and an air conditioning module 214. By means of this domain controller 210, for example, operating parameters of the in-vehicle functions can be collected from the sensors/actuators separately arranged on the vehicle body, and the operating preference data generated by the user during the use of the in-vehicle functions thus can be obtained.

The domain controller 220 for a chassis domain is, for example, connected to a chassis and suspension module of the vehicle in order to collect operating preference data related to a driving behavior and a charging state of the vehicle.

In addition, a plurality of indoor sensors 202, 203, 204 are connected to the vehicle bus 201, and these indoor sensors 202, 203, 204 are used for collecting the health level information in the cabin and feed it back to the vehicle bus. For example, PM2.5 concentration in the cabin can be detected by a PM2.5 sensor 202, air humidity in the cabin can be detected by an air humidity sensor 203, and vital signs of the user can be detected by an infrared sensor 204.

An integrated domain controller 230 is used for, for example, centralized processing and integrating of data from other domain controllers 210, 220 and from indoor sensors. According to one embodiment, the device 1 for intelligent health management of a cabin of a vehicle according to the disclosure may be arranged inside the vehicle, and thus arranged in the integrated domain controller 230 in such a manner that it is able to analyze a correlation between the operating preference data and the health level information within a determined time period, and thereby to further generate an adjustment strategy for at least one in-vehicle function.

A smart antenna module 240 is further connected to the vehicle bus 201 to allow sensor data integrated by the integrated domain controller 230 to be sent to a cloud 250 for analysis and processing. According to one embodiment, a device 1' for intelligent health management of a cabin of a vehicle according to the disclosure may also be arranged outside the vehicle and thus arranged in the cloud 250, so that it is not necessary to perform the intelligent health analysis locally in the vehicle, which saves the expenditure on software/hardware in the vehicle. After the cloud 250 completes the analysis, a result of the analysis may be output by the cloud to the mobile terminal 260 of the user so as to present the result to the user, for example, through a human-machine interface.

However, in the case where the device 1 is directly arranged in the vehicle locally, it is also possible to output the analyzed intelligent health report of the cabin via the smart antenna module 240 to the mobile terminal 260 of the user, so that the user can understand the relationship between his usage habits and the cabin health, and this also facilitates remote turning on or off of the corresponding in-vehicle functions by the user.

Figure 3:
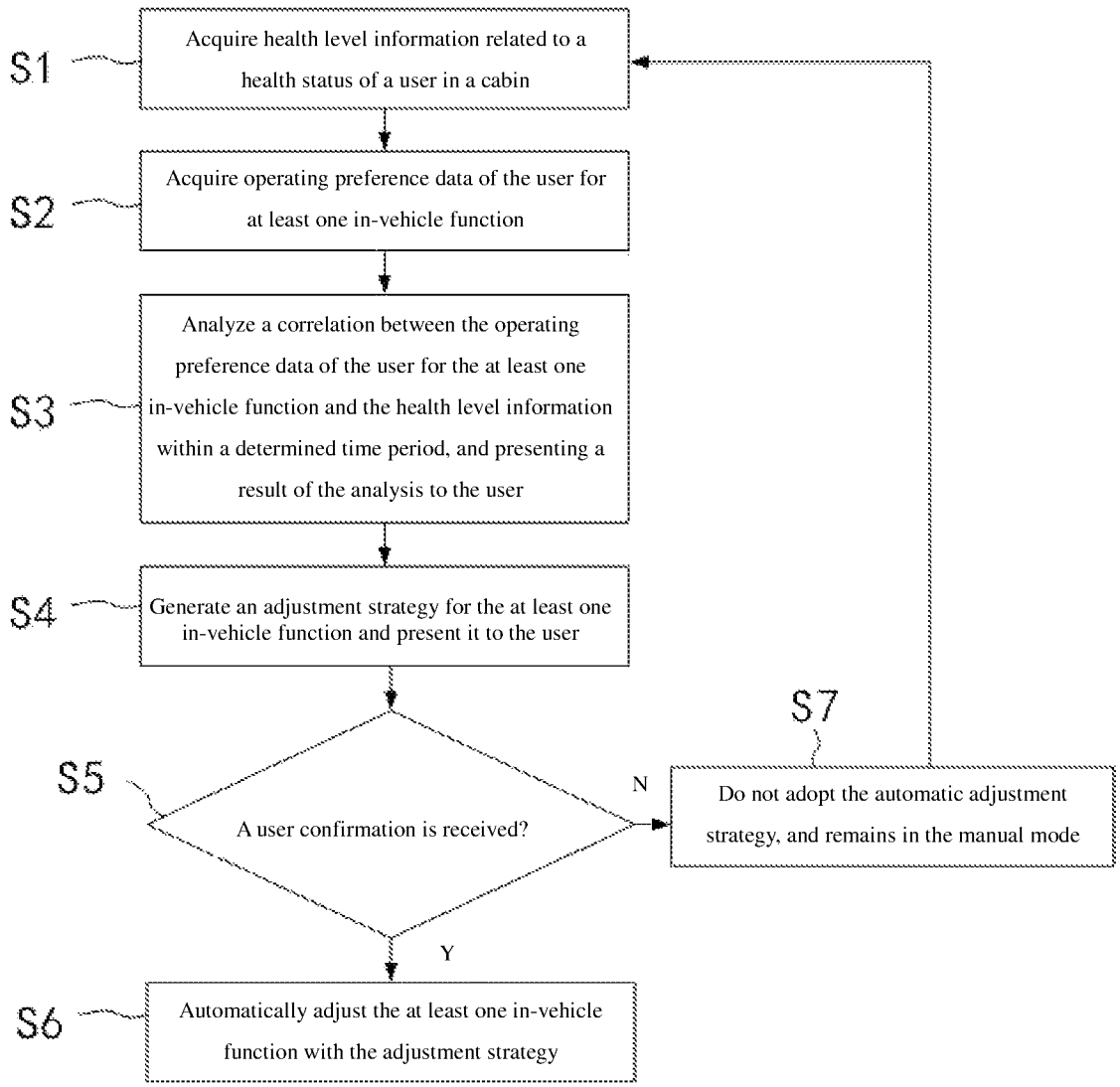
FIG. 3 shows a flowchart of a method for intelligent health management of a cabin of a vehicle according to an exemplary embodiment of the disclosure.

FIG. 3 shows a flowchart of a method for intelligent health management of a cabin of a vehicle according to an exemplary embodiment of the disclosure.

In step S1, health level information related to a health status of a user in the cabin is acquired. Here, the health level information comprises, for example, environmental level information and biological level information. Environmental level information is understood as at least one indoor environmental parameter potentially affecting the health status of the user in the cabin, which in particular comprises the temperature in the cabin, the air quality in the cabin, the pollen concentration in the cabin, the ultraviolet index in the cabin, the oxygen concentration in the cabin, the ultraviolet intensity in the cabin, and the humidity in the cabin. Biological level information is understood as biological parameters that can reflect the health status during the stay of the user in the cabin, which in particular comprises the infrared vital signs, the degree of attention and the visual fatigue of the user. As an example, health level information may be acquired in the form of a raw sensor signal and/or a grading result of the raw sensor signal.

In step S2, operating preference data of the user for at least one in-vehicle function is acquired. In the sense of the present disclosure, the operating preference data is understood as, for example, different operating states generated by various hardware and software that have been already equipped on the vehicle under the operating behaviors of different users. Such operating preference data comprises, for example: the number of times of activation, duration of use, frequency of use, time period of use, operating mode, operating temperature, operating angle, and operating intensity of at least one in-vehicle function (for example, pre-ventilation, pre-air conditioning, internal and external circulation, A/C air conditioning, vehicle windows, vehicle doors, sunroofs, seats, ambient lighting, etc.) by the user under certain external environmental conditions.

In step S3, a correlation between the operating preference data of the user for the at least one in-vehicle function and the health level information within a determined time period is analyzed, and a result of the analysis is presented to the user.

As an example, correlations may be analyzed individually for different areas (e.g., driver cabin, front passenger cabin, rear cabin) within the cabin. As another example, it is also possible to analyze correlations as a whole for the entire cabin area.

As an example, a degree of positive contribution and/or a degree of negative contribution of the operating preference data of the user to the health level information may be presented for different in-vehicle functions, and the operating preference data under different in-vehicle functions may be sorted as a function of a level of the positive or negative contribution degree, so that the user can have a clearer understanding of which of his operating habits causes the most notable impact on the health level in the cabin. Here, positive contribution means that, for example, the operating state or operating pattern of a specific in-vehicle function under the operating preference data can change the health level information in a direction that satisfies preset conditions or meets an eligibility standard. For example, closing vehicle windows and turning on the internal circulation of the vehicle under bad air condition have a positive contribution to the improvement of the air quality in the cabin. Negative contribution means that the operating state or operating pattern of a specific in-vehicle function under the operating preference data can change the health level information in a direction that deviates from preset conditions or violates an eligibility standard. For example, opening vehicle windows and frequently turning on the external circulation of the vehicle under bad air condition have a negative contribution to the improvement of the air quality in the cabin.

As an example, the correlation between the operating preference data of the user for each in-vehicle function and the health level information may be presented separately. This means, for example, when the oxygen concentration in the cabin is used as a health indicator, the user may, for example, be presented with the influence of "the number of times and the duration of opening vehicle windows" and "the number of times and the duration of opening external circulation", respectively, on the oxygen concentration in the cabin.

As another example, the correlations between the operating preference data of the user for multiple in-vehicle functions and the health level information may also be presented synergistically. This means, for example, when the oxygen concentration in the cabin is used as a health indicator, the user may, for example, be presented with the influence of a combined action of "the number of times and the duration of opening vehicle windows" and "the number of times and the duration of opening external circulation" on the oxygen concentration. During performing such a combined analysis, it is also advantageous to take into account mutual counteraction effects or mutual promotion effects between the operating states of different in-vehicle functions.

As another example, the correlation between each in-vehicle function and one type of health level information may be presented separately, or the correlations between each in-vehicle function and multiple types of health level information may be presented simultaneously.

As another example, the correlation may be presented in different time dimensions. For example, the correlation may be presented in a time dimension in the form of hours, days, weeks, months, quarters and/or years.

In step S4, an adjustment strategy for at least one in-vehicle function may be further generated based on the operating preference data and the health level information in a determined time period, and a confirmation from the user for this adjustment strategy is requested.

As an example, rationalization suggestions for user operating behaviors may be raised directly based on the correlations obtained from historical data. For example, if the user is used to seldom turning on the air conditioner or the internal/external circulation function during long-time driving and, as a result, the oxygen concentration in the cabin remains at a low level, and such an operating habit will cause adverse impacts on driver attention, etc., therefore, a suggestion may be given based on the analysis result to the user that it is recommended to roll down the vehicle windows or turn on the internal/external circulation as appropriate during long-time driving in the future.

As another example, an automatic adjustment strategy for at least one in-vehicle function may also be generated according to the current environmental information or the environmental information in the coming future (e.g., weather, temperature, ultraviolet intensity, pollen dispersion, air quality) outside the vehicle.

In the next step S5, whether a confirmation operation from the user for the adjustment strategy is received may be determined.

If a user confirmation is received, the adjustment strategy can be applied in step S6, and automatic adjustment of at least one in-vehicle function is realized.

If no user confirmation is received within a determined time period or information that the user refuses to accept is received, the recommended adjustment strategy may not be adopted in step S7 and as a result, the manual adjustment mode may be continued.

Figure 4:
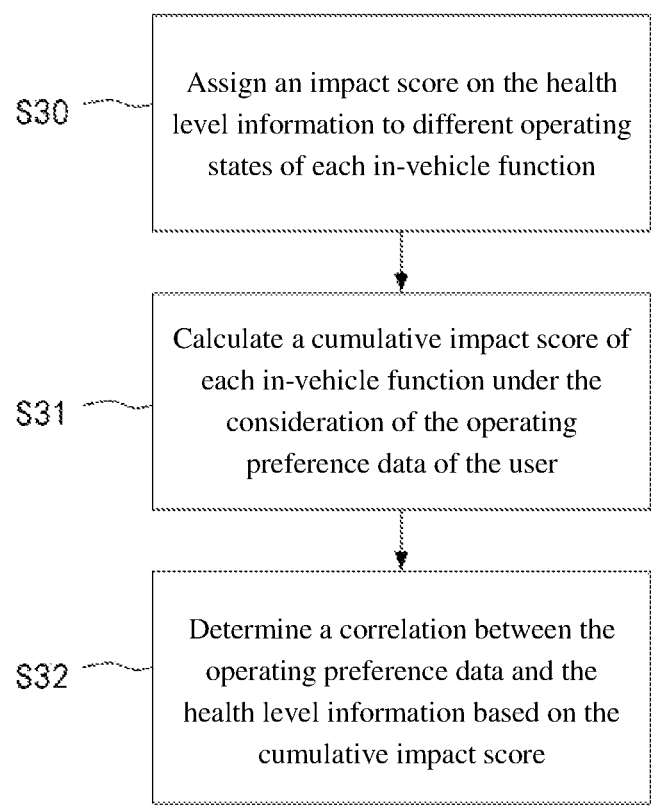
FIG. 4 shows a flowchart of an exemplary embodiment of a step of the method shown in FIG. 3.

FIG. 4 shows a flowchart of an exemplary embodiment of a step S3 of the method shown in FIG. 3. The step S3 exemplarily comprises steps S30-S32.

In step S30, an impact score on the health level information is pre-assigned to different operating states of each in-vehicle function. In this case, it can be done, for example, by means of a manual labeling process, but it may also be derived on the basis of specific mathematical models. As an example, concerning the health level information "suitable indoor temperature" in winter, for the sunroof function, a score "−1" may be assigned to a state of "single opening of sunroof", and a score "−1" may be assigned to a state of "sunroof opening for 1 minute"; for the air conditioner function, a score "+1" may be assigned to a state of "single turning on of air-conditioning for heating", and a score "+1" may be assigned to a state of "turning on air-conditioning for heating for 1 minute"; and for the seat heating function, a score "+1" may be assigned to a state of "single turning on of seat heating", and so on.

In step S31, a cumulative impact score of each in-vehicle function under the consideration of the operating preference data of the user is calculated. Here, for example, for the time of a month, it is counted that the user turned on the air conditioner for heating for ten times in total, and an average duration of which is 30 minutes, so that a cumulative score "40", for example, is obtained for "air-conditioning function".

In step S32, the correlation between the operating preference data and the health level information is determined based on the cumulative impact score. As an example, a level of correlation can be directly shown in the form of cumulative score: the larger the score, the greater the correlation. As another example, different grading thresholds may be additionally set and the obtained cumulative impact score may be compared with each grading threshold so as to qualitatively determine the level of correlation between the operating preference data and the health level information.

It is worth noting that the above-mentioned embodiment only introduces the correlation between the operating preference data and one type of health level information (or to say one health indicator). However, it is also possible to comprehensively analyze the correlations between the operating preference data and various types of health level information. For example, for the first health level information, "suitable indoor temperature", the cumulative score of the operating preference data of the user for the air-conditioning function is "40", while for the second health indicator "excellent indoor air quality", the cumulative score of the operating preference data of the user for the air-conditioning function is only "5". Therefore, it is meaningful to average or weight the cumulative scores corresponding to certain in-vehicle functions for all types of health level information, so that the correlation between the operating preference data of the user and the overall health level in the cabin can be obtained.

Figure 5:
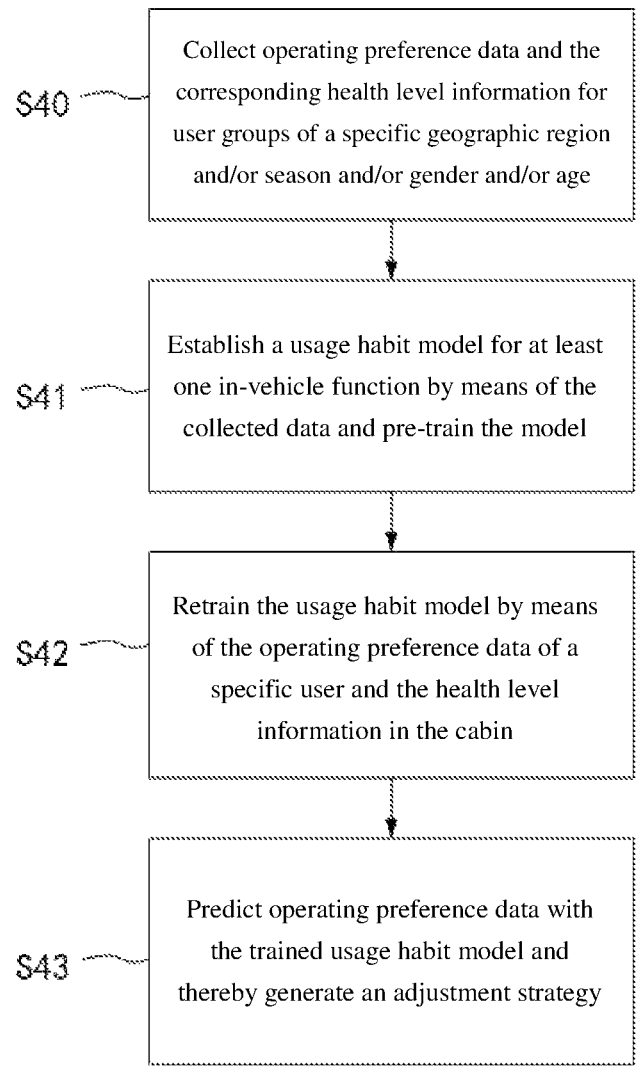
FIG. 5 shows a flowchart of an exemplary embodiment of a step of the method shown in FIG. 3.

FIG. 5 shows a flowchart of an exemplary embodiment of a step S4 of the method shown in FIG. 3. The step S4 exemplarily comprises steps S40-S43.

In step S40, crowdsourced operating preference data and corresponding crowdsourced health level information may be collected in a crowdsourcing manner, for example, for vehicle user groups of a specific geographic region and/or a specific season and/or a specific gender and/or a specific age. This can be achieved in particular with the help of a shared cloud platform based on big data. Take Beijing and Shanghai as examples for comparison. Significant climatic differences exist between the two due to their geographical differences. Therefore, users in these two regions also have differences in the usage habits of in-vehicle functions, such as air conditioning, ventilation, and seat heating. In this case, it makes sense to collect relevant data separately for users in Beijing and Shanghai and use the data for the subsequent analysis.

In step S41, a usage habit model for at least one in-vehicle function may be established by means of the collected data and be pre-trained. Here, input-output mapping of the machine learning model is established, for example, using the operating preference data based on big data and the health level information as training data. The purpose of this is to enable the machine learning model to simulate perceptions of various environmental factors in the human brain to form logical relationships between various perceptions and the health level, so that when given external environmental information (such as the temperature, humidity, air quality, etc. outside the vehicle) is input into the model, for example, an adjustment strategy for at least one in-vehicle function can be automatically output. The result of such output, in one aspect, takes into account an expected operating behavior (such as adjusting the air conditioner to a preset temperature or opening the vehicle window) of the user group for this environmental factor or physical state, and meanwhile further takes into account the influence of the operating behaviors of the user on the health level in the cabin, so the model is allowed to seek a balance between user comfort and the health level in the cabin through a continuous iterative training process, and a final adjustment strategy can be obtained while taking into account both as much as possible. As an example, different usage habit models may be established and pre-trained for user groups of different geographic regions, seasons, genders and/or ages, and these usage habit models are pre-stored in the cloud platform so as to be retrieved in different scenarios.

In step S42, the preliminary usage habit model established in step S41 is retrained by means of the operating preference data of a specific user and the health level information. In order to achieve a more accurate matching of the pre-trained model with the habits of individual users, kernel functions or internal parameters of the model can be finely adjusted with the help of the data of an individual user. As an example, a usage habit model is pre-trained based on the big data analysis of a specific region and season to adapt to "common behaviors" of the users from the same region and season. For example, the air conditioner is pre-programmed, based on big data, to be automatically adjusted to 24 degrees in spring and when the outdoor temperature reaches 30 degrees, and the 24 degrees is generated based on the air-conditioner adjusting operation of 100,000 users during this period. This "common behavior" is then specifically adjusted using behavioral differences of individual users. For example, if a particular user feels that 24 degrees is too hot and manually adjusts it to 22 degrees, then after 2 to 3 times of manual adjustment, the "artificial brain" will relearn and remember 22 degrees instead of 24 degrees.

In S43, operating preference data is predicted using the trained usage habit model and an adjustment strategy is thereby generated. Here, for example, certain external environment information and/or current health level information in the cabin is input into the usage habit model, and then the usage habit model can output the predicted operating preference data based on an overall consideration of logical relationships between various constraints, and such predicted operating preference data in particular enables the health level information in the cabin to meet preset conditions.

Figure 6:
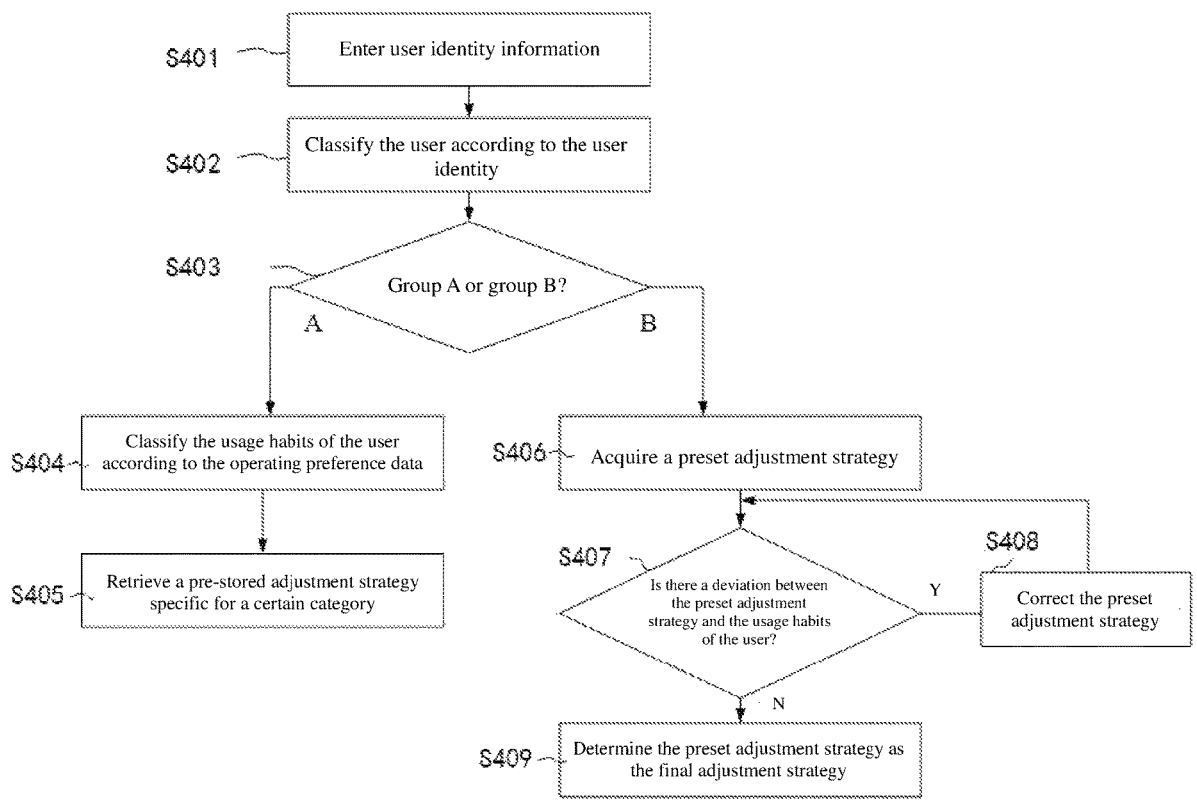
FIG. 6 shows a flowchart of an exemplary embodiment of a step of the method shown in FIG. 3.

FIG. 6 shows a flowchart of an exemplary embodiment of a step S4 of the method shown in FIG. 3. The step S4 exemplarily comprises steps S401-S409.

In step S401, user identity information is entered. This can be achieved by means of, for example, a specific user information acquisition module (e.g., a face recognition module, a voice recognition module, an identity information input module, an identity identification recognition module and/or an iris recognition module).

In step S402, the user is preliminarily classified according to the user identity. As an example, a vehicle model purchased by the user may be identified or historical maintenance records may be retrieved according to the user identity, thereby estimating a consumption ability of the user. As another example, the age and the gender of the user may be identified according to the user identity, thereby estimating an approximate level of physical fitness. As another example, a payment status or purchased version of the user for a specific vehicle function can be retrieved according to the user identity, so that the permission of use of additional functions for the user can be known.

In step S403, it is determined whether the user belongs to group A or group B according to the result of preliminary classification. Here, group A represents, for example, a group of users who purchase a "low-level version" of the cabin health management function, and group B represents, for example, a group of users who purchase a "premium version" of the cabin health management function. Compared with the "low-level version" cabin health management function, the functions of the "premium version" can achieve, for example, a better adaptation of the automatic adjustment strategy to the operating habits of the user, provide an automation solution that is more in line with the operating style or preference of the user, and contain more types of health parameter records.

If it is determined that the user identity belongs to group A, an adjustment strategy may then be generated, for example, with a first mode. Therefore, in step S404, the operating preference data within a period of time can be recorded and the usage habits of the user can be classified based on this.

Next, in step S405, a pre-stored adjustment strategy specific for a certain usage habit category may be retrieved from the cloud platform or locally according to a result of the classification. For example, if it is determined that the user has a "preference for warm" in the usage habit of air-conditioner, an adjustment strategy for the air conditioner function then can be retrieved from this group;

conversely, another adjustment strategy for the air conditioner function can be retrieved from a database of "preference for cold".

If it is determined that the user belongs to group B, an adjustment strategy may be generated, for example, in a second mode. Therefore, in step S406, a preset adjustment strategy may be obtained from a cloud database or system background. This adjustment strategy, for example, may be established for this vehicle model during the development phase and stored by default.

Then in step S407, it is checked in real time whether there is a deviation between the preset adjustment strategy and the usage habits of the user. In order to be able to identify such deviations, a feedback event of the user to the adjustment strategy may be recorded, comprising: manual adjustment of the operating state of at least one in-vehicle function by the user. It can be understood that if the user is satisfied with the currently applied adjustment strategy, or to say he thinks that the current adjustment strategy conforms to his personal operating habits, then the user generally does not manually intervene in the automatic adjustment process. Conversely, if the user is not satisfied with the current automatic adjustment strategy, he will intervene in the automatic adjustment process by manual adjustment (e.g., overriding). By recording the number of times and the frequency of these feedback events, the deviation between the adjustment strategy and the usage habits of the user can be determined. Here, it is also possible to determine a direction of corrective tendency of the adjustment strategy for at least one in-vehicle function based on the feedback event.

If it is determined that there is a deviation, the current preset adjustment strategy may be corrected in step S408 to reduce the deviation. For example, if the user manually changes a current air outlet direction, the air outlet direction then can be stored as new operating preference data, and a new adjustment strategy can be generated based on this.

If it is determined that there is no deviation, the preset adjustment strategy may be determined and stored as the final adjustment strategy in step S409, so that this adjustment strategy can be directly invoked during the use of the vehicle by the user next time.

It should be noted that although in this example the generation processes of the first and second adjustments are performed independently of each other, it is also conceivable that the first mode is performed as a basic adjustment mode prior to the second mode. Furthermore, other combined embodiments of the two modes are also possible.

Figure 7:
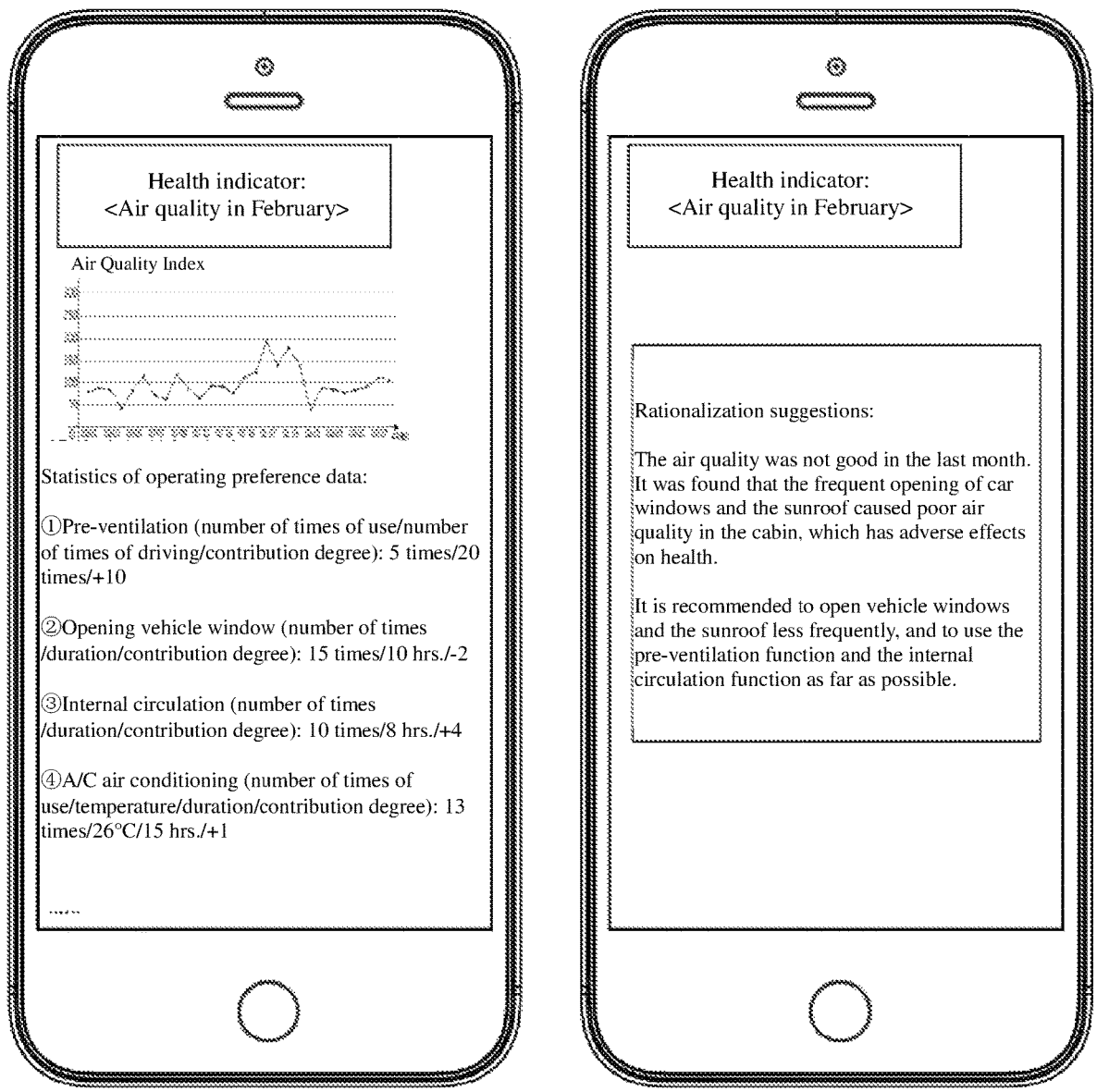
FIG. 7 shows illustrative user interfaces for presenting results of a cabin health analysis to a user according to an exemplary embodiment.

FIG. 7 shows illustrative user interfaces for presenting results of a cabin health analysis to a user according to an exemplary embodiment. The user interface shown here may be, for example, a part of a mobile terminal of the user, by means of which mobile terminal, data and analysis reports from a device for cabin intelligent health management can be received, and at the same time, input instructions of the user can also be transmitted via the mobile terminal to the device or to various software/hardware actuators on the vehicle.

As shown on the left side of FIG. 7, the correlations between an exemplary type of health level information with multiple types of operating preference data are displayed on the user interface. In this example, the user is presented with the air quality in the cabin in the past month (e.g., February), and this health level information is shown, for example, in the form of a graph. The operating preference data of the user for different in-vehicle functions as well as the correlation between the operating preference data and the health level information are respectively shown below the graph.

For example, concerning the pre-ventilation function of the vehicle, it is shown that the number of times of driving in the past month is 20, during which period the number of times of using the pre-ventilation function is 5, and the contribution degree of the operating preference data to the above health level information is integrally calculated as +10.

Operating preference data is shown in different analysis dimensions concerning the vehicle window function. Here, for example, the number of times and the total duration (or single duration on average) of opening vehicle windows in the past month are respectively shown, and a total contribution degree of this in-vehicle function to the health level information is also shown.

In addition, the operating preference data and the corresponding contribution degrees for the past month are also shown for internal circulation and A/C air conditioning functions, respectively.

Rationalization suggestions generated for the analysis result are shown on the right side of FIG. 7. Here, for example, it is found based on the analysis of historical data that frequent opening of vehicle windows and sunroofs by the user for a few days has caused poor overall air quality in the cabin; thus, a suggestion may be raised to the user: the air quality was not good in the last month, and it was found that the frequent opening of vehicle windows and sunroofs caused poor air quality in the cabin, which has adverse effects on health.

As an alternative to the act of opening vehicle windows and sunroofs, the user may also be advised as follows: it is recommended to open vehicle windows and sunroofs less frequently, and to use the pre-ventilation function and the internal circulation function more, which can as well block the polluted air and keep the indoor air clean during long-time driving.

Figure 8:
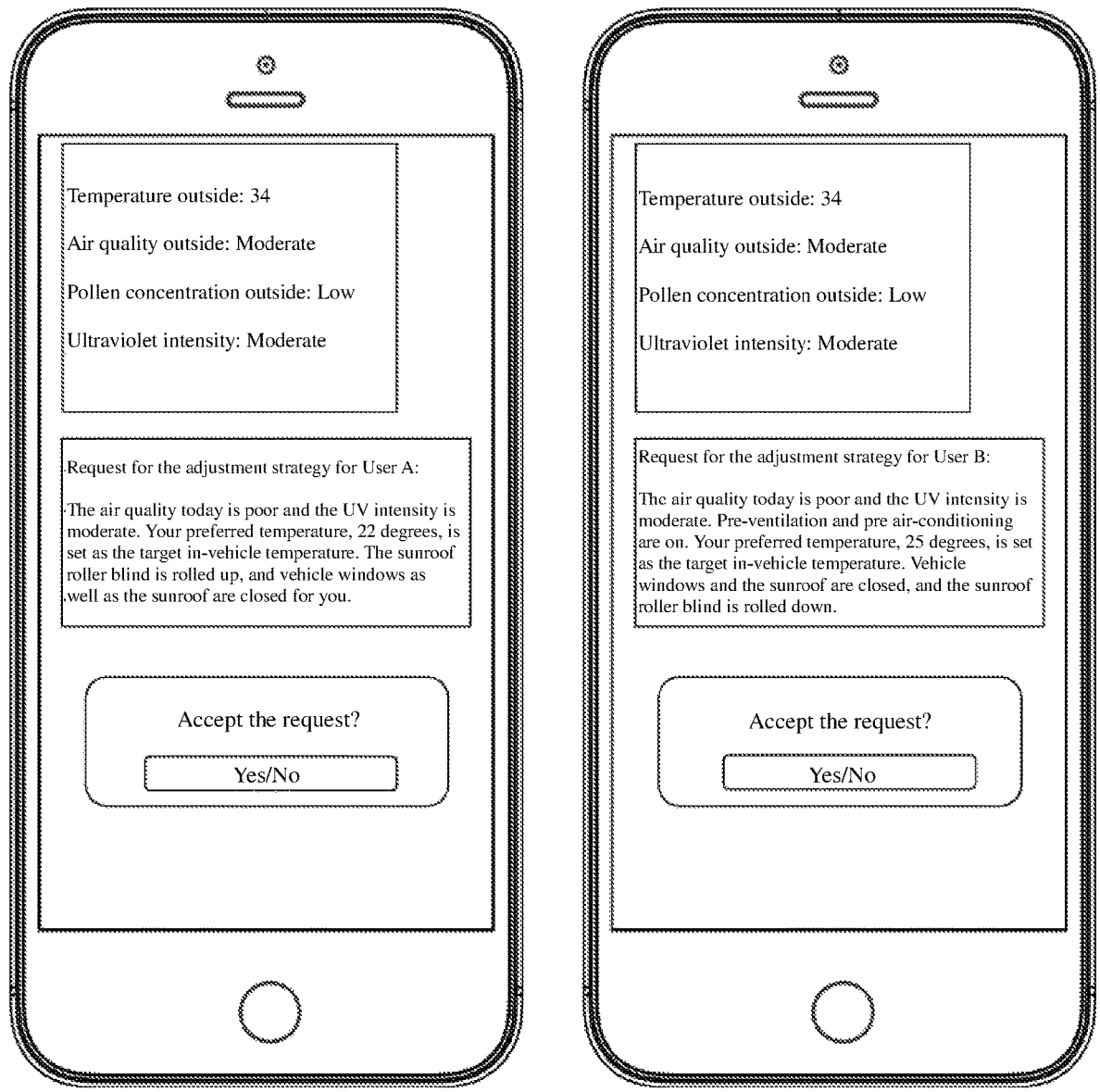
FIG. 8 shows illustrative user interfaces for presenting adjustment strategies to different users according to an exemplary embodiment.

FIG. 8 shows illustrative user interfaces for presenting adjustment strategies to different users according to an exemplary embodiment.

Here, the adjustment strategies generated by the method according to the disclosure are shown, for example, for two users A and B, respectively. The results of health analysis show that the two users have different perceptions of the environment, which leads to differences in their usage habits and operating preferences for in-vehicle functions. For example, for the same external environmental factors "outside air temperature: 34 degrees, summer, moderate air pollution, low pollen concentration, relatively high level of ultraviolet intensity", user A has a preference for "22 degrees" as the indoor temperature and likes opening sunroofs and vehicle windows, while user B prefers "25 degrees" as the indoor temperature and internal air circulation, and requires sun protection.

The adjustment strategy for user A is shown on the left side of FIG. 8, "The air quality today is poor and the UV intensity is high. Your preferred temperature, 22 degrees, is set as the target in-vehicle temperature. The sunroof roller blind is rolled up, and vehicle windows as well as the sunroof are closed for you." As can be seen, although it is concluded from historically collected operating preference data that user A usually prefers to open vehicle windows and the sunroof, the trained usage habit model further takes into account the health level in the cabin; thus, the finally generated adjustment strategy partially contradicts the original habits of the user, though the behavioral preferences of the user are taken into consideration, so that a good health level in the cabin on the whole can be guaranteed.

The adjustment strategy for user B is shown on the right side of FIG. 8, "The air quality today is poor and the UV intensity is high. Your preferred temperature, 25 degrees, is set as the target in-vehicle temperature. Vehicle windows and the sunroof are closed for you, and the sunroof roller blind is rolled down." It can be seen that since user A and user B have different individual operating habits under the same external environmental conditions, there are differences in the adjustment strategies formulated therefor.

Meanwhile, a request for user confirmation is also shown in the user interface in FIG. 8, thereby ensuring that the automatic adjustment mode is turned on only if a user confirmation is received.

Although specific embodiments of the disclosure are described in detail here, these embodiments are for the purpose of explanation only and should not be considered as limitations to the scope of the disclosure. Various substitutions, alterations and modifications can be devised without deviating from the spirit and scope of the disclosure.

The invention claimed is:

1. A method for intelligent health management of a cabin of a vehicle, comprising the steps of:
   S1: acquiring health level information related to a health level in the cabin by a first acquisition module (10);
   S2: acquiring operating preference data of a user in the cabin for at least one in-vehicle function by a second acquisition module (20); and
   S3: analyzing a correlation between the operating preference data of the user for the at least one in-vehicle function and the health level information within a determined time period by an analysis module (30) in a cabin health analysis, and presenting a result of the cabin health analysis to the user.

2. The method according to claim 1, wherein the health level information is acquired in a form of a raw sensor signal and/or a grading result of the raw sensor signal.

3. The method according to claim 1, wherein the health level information comprises environmental level information and biological level information, wherein the environmental level information is at least one of a temperature in the cabin, an air quality in the cabin, a pollen concentration in the cabin, an ultraviolet index in the cabin, an oxygen concentration in the cabin and a humidity in the cabin, and wherein the biological level information is at least one of an infrared vital sign, a degree of attention, and a visual fatigue of the user.

4. The method according to claim 1, wherein the operating preference data is at least one of a number of times of activation, a duration of use, a frequency of use, a time period of use, an operating mode, an operating temperature, an operating angle, and an operating intensity of at least one in-vehicle function by the user under corresponding external environmental conditions.

5. The method according to claim 1, wherein step S3 comprises:
   pre-assigning an impact score on the health level information to different operating states of each in-vehicle function;
   calculating a cumulative impact score of each in-vehicle function under a consideration of the operating preference data of the user; and
   determining the correlation based on the cumulative impact score.

6. The method according to claim 1, wherein step S3 comprises:
   presenting a degree of positive contribution and/or a degree of negative contribution of the operating preference data of the user to the health level information for different in-vehicle functions.

7. The method according to claim 1, wherein step S3 comprises:
   presenting separately the correlation between the operating preference data of the user for each in-vehicle function and the health level information; and/or
   presenting synergistically the correlation between the operating preference data of the user for a plurality of in-vehicle functions and the health level information.

8. The method according to claim 1, wherein step S3 comprises:
   presenting the correlation in different time dimensions, wherein the correlation is presented in a time dimension in a form of days, weeks, months, quarters and/or years.

9. The method according to claim 1, further comprising the steps of:
   generating an adjustment strategy for at least one in-vehicle function according to the operating preference data and the health level information in a determined time period; and
   presenting the adjustment strategy to the user and/or adjusting automatically the at least one in-vehicle function with the adjustment strategy.

10. The method according to claim 9, wherein the at least one in-vehicle function is automatically adjusted with the adjustment strategy only when a user confirmation of the adjustment strategy is received.

11. The method according to claim 1, further comprising the steps of training a usage habit model of the user for at least one in-vehicle function by the operating preference data of the user and the health level information in the cabin, wherein the trained usage habit model is used to predict operating preference data that enables the health level information in the cabin to meet preset conditions under corresponding external environmental conditions, and generating an adjustment strategy for the at least one in-vehicle function based on the predicted operating preference data.

12. The method according to claim 11, wherein prior to the training, pre-training the usage habit model based on big data by crowdsourced operating preference data of user groups of a specific geographic region and/or of a specific season and/or of a specific gender and/or of a specific age as well as corresponding crowdsourced health level information.

13. The method according to claim 9, wherein the adjustment strategy is generated with a first mode and/or a second mode, wherein in the first mode, usage habits of the user are classified based on the operating preference data of the user and a predefined adjustment strategy is retrieved according to a result of the classification, and in the second mode, it is checked whether there is a deviation between the predefined adjustment strategy and the usage habits of the user, and the predefined adjustment strategy is corrected in response to the deviation so as to reduce the deviation.

14. The method according to claim 13, wherein it is checked whether there is the deviation by recording a feedback event of the user on the adjustment strategy, the feedback event comprising a manual adjustment of the operating state of at least one in-vehicle function by the user.

15. The method according to claim 9, further comprising the steps of:
   storing the adjustment strategy in a cloud and/or locally for an identity of the user; and retrieving a corresponding adjustment strategy from the cloud and/or locally when the identity of the user is identified.

16. A device (1) for intelligent health management of a cabin of a vehicle, wherein the device (1) is configured to perform the method according to claim 1, the device (1) comprising:
- a first acquisition module (10) configured to acquire health level information related to a health level in the cabin;
- a second acquisition module (20) configured to acquire operating preference data of a user in the cabin for at least one in-vehicle function; and
- an analysis module (30) configured to analyze a correlation between the operating preference data of the user for the at least one in-vehicle function and the health level information within a determined time period in a cabin health analysis, and to present a result of the cabin health analysis to the user.

* * * * *